United States Patent [19]

Sepponen

[11] Patent Number: 5,146,924
[45] Date of Patent: Sep. 15, 1992

[54] ARRANGEMENT FOR EXAMINATION OF A MATERIAL

[75] Inventor: Raimo E. Sepponen, Helsinki, Finland

[73] Assignee: Instrumentarium Corp., Finland

[21] Appl. No.: 400,461

[22] Filed: Aug. 29, 1989

[30] Foreign Application Priority Data

Sep. 12, 1988 [FI] Finland .................. 884174

[51] Int. Cl.⁵ .............................................. A61B 5/055
[52] U.S. Cl. ............................. 128/653.2; 128/660.01; 324/309; 324/316
[58] Field of Search ....... 128/653 A, 653 CA, 660.01; 324/307, 309, 316

[56] References Cited

U.S. PATENT DOCUMENTS

| | | | |
|---|---|---|---|
| 3,798,532 | 3/1974 | Hausser | 324/316 |
| 4,543,959 | 10/1985 | Sepponen | 128/653 A |
| 4,719,425 | 1/1988 | Ettinger | 128/653 A |
| 4,984,573 | 1/1991 | Leunbach | 128/653 CA |

FOREIGN PATENT DOCUMENTS

3421045 12/1985 Fed. Rep. of Germany ... 128/653 A

OTHER PUBLICATIONS

Lepley, AR and Closs, GL, "Chemically Induced Magnetic Polarization", New York, 1973, pp. 1-3, 36-43, 88-97, 134-139, 190-197, 220-227, 270-283, 320-327, and 378-385.

Lurie DJ, Bussel, DM, Bell, LH, Mallard, JR, "Proton Electron Double Resonance Imaging: A new method for imaging free radicals", Proc. S.M.R.M. Fifth Annual Meeting, 1987, New York, p. 24.

Lurie, DJ, Bussel, DM, Bell, LH, Mallard, JR, "Proton-Electron Double Magnetic Imaging of free radical solutions", J. Magn. Reson., vol. 76, 1988, pp. 366-370.

Röschmann, P., "Radiofrequency penetration and absorption in the human body: Limitations to high-field whole-body nuclear magnetic resonance imaging", Med. Phys. 14, 1987, pp. 922-931.

Tenforde, T. S. and T. F. Budinger, "Biological Effects and Physical Safety Aspects of NMR Imaging and in Vivo Spectroscopy", University of California, Berkeley, pp. 510-516; 521-522.

Potenza, J., "Measurement and Applications of Dynamic Nuclear Polarization", Adv. Mo. Relaxation Processes, vol. 4, pp. 229-354, 1972.

*Primary Examiner*—Lee S. Cohen
*Assistant Examiner*—K. M. Pfaffle
*Attorney, Agent, or Firm*—Andrus, Sceales, Starke & Sawall

[57] ABSTRACT

An apparatus for the examination of an object, such as a human body, by means of ultrasound and NMR methods in such a manner that both examination methods are adapted to be effected substantially simultaneously and on the same target area. The apparatus is provided with a device for radiating the magnetization of an electron spin system in the said target area in order to achieve a dynamic nuclear polarization and to amplify an NMR signal through a so-called Overhauser-phenomenon.

4 Claims, 7 Drawing Sheets

ARRANGEMENT FOR EXAMINATION OF A MATERIAL

FIELD OF THE INVENTION

The present invention relates to an arrangement for examination of an object, such as a human body, an animal, a tree trunk or a food product.

BACKGROUND OF THE INVENTION

Magnetic resonance imaging (MRI) is a technique which utilizes the nuclear magnetic resonance phenomenon (NMR) for discovering the local distributions of the nuclear density and nucleus-related NMR characteristics of an object and the physical and chemical characteristics affecting the same. Said NMR characteristics include e.g.: longitudinal relaxation (characterized by longitudinal relaxation time T1), transverse relaxation (characterized by transverse relaxation time T2), relaxation in a rotating frame of reference (characterized by relaxation time T1rho), chemical shift, nuclear coupling factors and, physical phenomena affecting the NMR characteristics, such as: flow, diffusion, paramagnetic substances, ferromagnetic particles, viscosity and temperature.

Methods and applications of magnetic resonance imaging have been described in a number of references: Poole CP and Farach HA: Theory of magnetic resonance, John Wiley, New York, 1987, Stark DD and Bradley WG: Magnetic resonance imaging, C. V. Mosby Comp., St. Louis 1988, Gadian DG: Nuclear magnetic resonance and its applications to living systems, Oxford Univ. Press, London 1982, Shaw D: Fourier transform NMR spectroscopy, Elsevier, Amsterdam, 1984, Battocletti JH: NMR proton imaging, CRC Crit. Rev. Biomed. Eng. vol. 11, pp. 313-356, 1984, Mansfield P and Morris PG: NMR imaging in biomedicine, Adv. in magnetic resonance, Academic Press, New York 1982, Abragam A: The principles of nuclear magnetism, Clarendon Press, Oxford 1961, Lasker SE and Milvy P (eds.): Electron spin resonance and nuclear magnetic resonance in biology and medicine and magnetic resonance in biological systems, Annals of New York Academy of Sciences vol. 222, New York Academy of Sciences, New York 1973, Sepponen RE: Discrimination and characterization of biological tissues with magnetic resonance imaging: A study on methods for T1, T2, T1rho and chemical shift imaging, Acta Polytechnica scandinavica EL-56, Helsinki 1986, Fukushima E and Roeder SB: Experimental pulse NMR, Addison Wesley, London 1981, Anderson W et al: U.S. Pat. No. 3,475,680, Ernst RR: U.S. Pat. No. 3,501,691, Tomlinson BL et al: U.S. Pat. No. 4,034,191, Ernst RR: U.S. Pat. No. 3,873,909, Ernst RR: U.S. Pat. No. 4,070,611, Bertrand RD et al: U.S. Pat. No. 4,345,207, Young IR: U.S. Pat. No. 4,563,647, Hofer DC et al: U.S. Pat. No. 4,110,681, Savelainen MK: Magnetic resonance imaging at 0.02 T: Design and evaluation of radio frequency coils with wave winding, Acta Polytechnica Scandinavica Ph 158, Helsinki 1988, Sepponen RE: U.S. Pat. No. 4,743,850, Sepponen RE: U.S. Pat. No. 4,654,595, Savelainen MK: U.S. Pat. No. 4,712,068, Sepponen RE: U.S. Pat. No. 4,587,493, Savelainen MK: U.S. Pat. No. 4,644,281 and Kupiainen J: U.S. Pat. No. 4,668,904.

Dynamic nuclear polarization (DNP) has been describe e.g. in the following references: Lepley AR and Closs GL: Chemically induced magnetic polarization, Wiley, New York 1973, Potenza J: Measurement and Applications of dynamic nuclear polarization, Adv. Mol. Relaxation Processes vol. 4, Elsevier, Amsterdam 1972, pp. 229-354, Ettinger KV: U.S. Pat. No. 4,719,425.

DNP is a magnetic double resonance method which thus requires two separate spin populations. Such spin populations include e.g. the spins of electrons and protons. In a double resonance method, the distribution of one spin population on various energy levels is varied and the other spin population is monitored. As certain conditions are fulfilled, the resonance signal of a spin population being monitored becomes amplified (Overhauserphenomenon). The amplitude of an amplified signal can be several hundred times higher than a non-amplified signal. The amplification factor may be positive or negative. The amplified signal is characteristically highly sensitive to the physico-chemical conditions and reactions of a spin environment, and, thus, has an obvious application for the examination of the chemical properties of a material.

The reference Ettinger KV: U.S. Pat. No. 4,719,425 discloses as applications the mapping of the contents of paramagnetic components and the mapping of the activity of cerebral nerve cells. In references Lurie DJ, Bussel DM, Bell LH, Mallard JR: Proton Electron Double Resonance Imaging: A new method for imaging free radicals, Proc. S.M.R.M. Fifth Annual Meeting, 1987, New York, p. 24 and Lurie DJ, Bussel DM, Bell LH, Mallard JR: Proton-Electron Double Magnetic Resonance Imaging of free radical solutions, J. Magn. Reson., vol. 76, 1988, pp. 366-370 discloses as possible applications the mappings of free radical groups, nitroxide radicals and oxidation degree.

A problem in the prior art is the absorption of ESR frequency electromagnetic oscillation in an object being examined. This leads to two major drawbacks: 1. The saturation on ESR frequency only occurs in those parts of an object which are near the radiator (for example, the penetration depth of 1.12 GHz in a muscular tissue is less than 3 cm). 2. Since the ESR line has a relatively great width, the saturation requires the use of high power which, on absorbing in an object, may result in the damage to the object (heating).

The interaction of electromagnetic radiation and biological tissue has been described e.g. in the following references: Röschmann P: Radiofrequency penetration and absorption in the human body: Limitations to high field whole body nuclear magnetic resonance imaging, Med. Phys. 14 (6), pp. 922-931, 1987, Tenforde TS and Budinger TF: Biological effects and physical safety aspects of NMR imaging and in vivo spectroscopy, in Thomas SR and Dixon RL (eds.) NMR in medicine: The instrumentation and clinical applications, Medical Physics Mcnograph No. 14, American Institute of Physics, New York 1986.

According to the reference Sepponen: U.S. Pat. No. 4,543, 959, it is prior known to combine NMR and ultrasonic imaging method. In the arrangement disclosed in the reference, the actual imaging is effected with ultrasound which is capable of real-time imaging and NMR examination is effected on a desired target area. The localization of a target or object area is effected by using methods known in magnetic imaging, such as a selective excitation in connection with magnetic field gradients as well as so-called Fourier methods for mapping the density distribution in the direction of a gradient field. A problem in the technical realization of this method is the generation of a relatively powerful magnetic field required by the NMR method in a manner that the ultrasonic examination can be readily effected.

SUMMARY OF THE INVENTION

By means of the invention set out in the claims it is possible to avoid the prior art drawbacks and to design an examination apparatus which combines the benefits of ultrasound and DNP as well as NMR.

The objects of the invention are achieved as set forth in more detail in claim 1 and in the subclaims.

BRIEF DESCRIPTION OF THE DRAWINGS

The invention will now be described more detail with reference made to the accompanying drawings, in which.

DETAILED DESCRIPTION OF THE INVENTION

Figure 1:
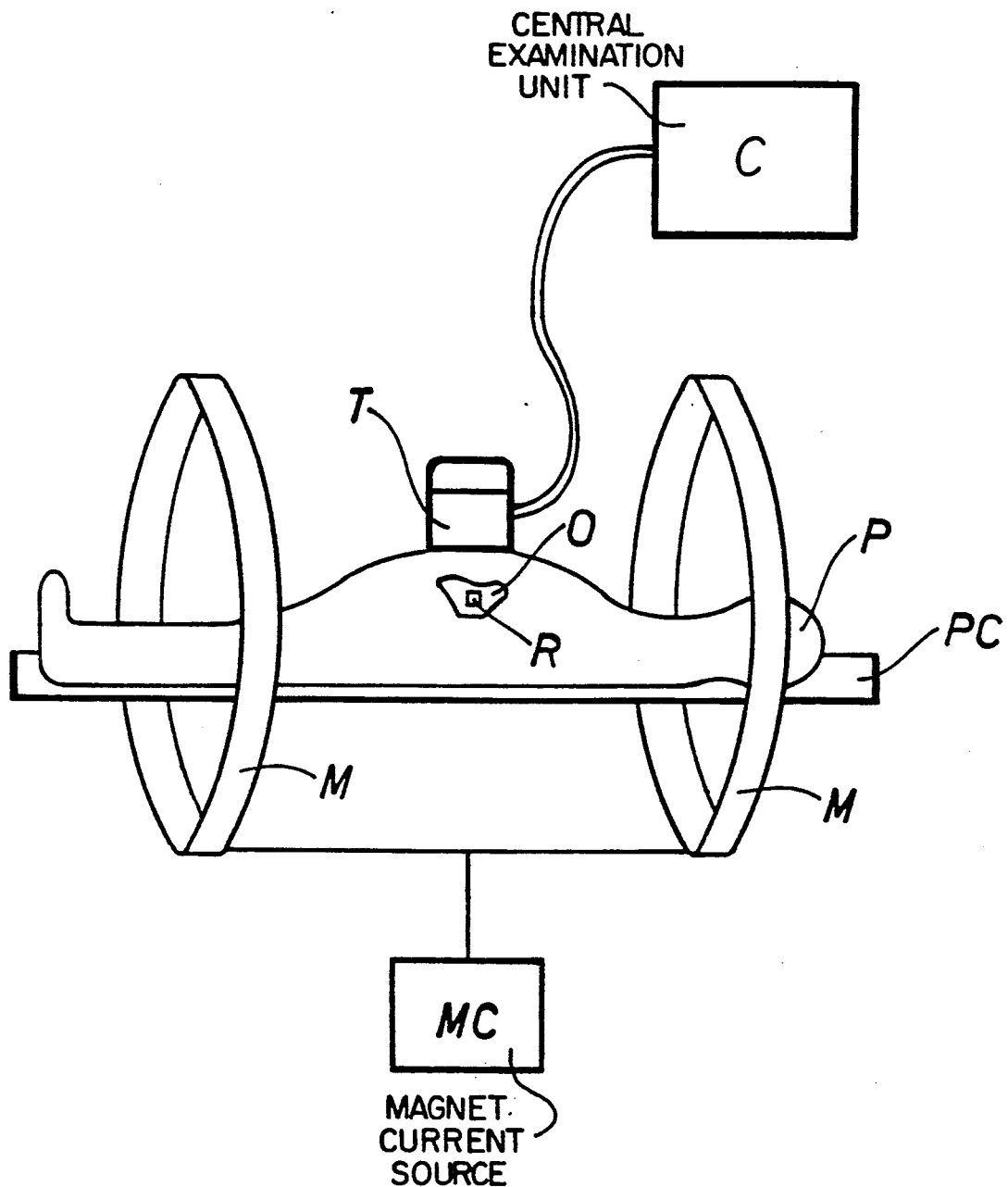
FIG. 1 shows the main components of an examination apparatus.

FIG. 1 shows a magnet M required for the generation of a polarizing magnetic field Bo and a source of magnet current MC connected therewith. Magnet M can be a resistive, permanent or superconductive magnet. As for its geometry, magnet M can be Helmholz, solenoid, spherically symmetrical etc. a patient P lies on a hospital bed or a support PC. A sensor T of the examination apparatus is used to localize and examine a region R of interest in an organ O. Sensor T is connected to a central examination unit C.

Figure 2:
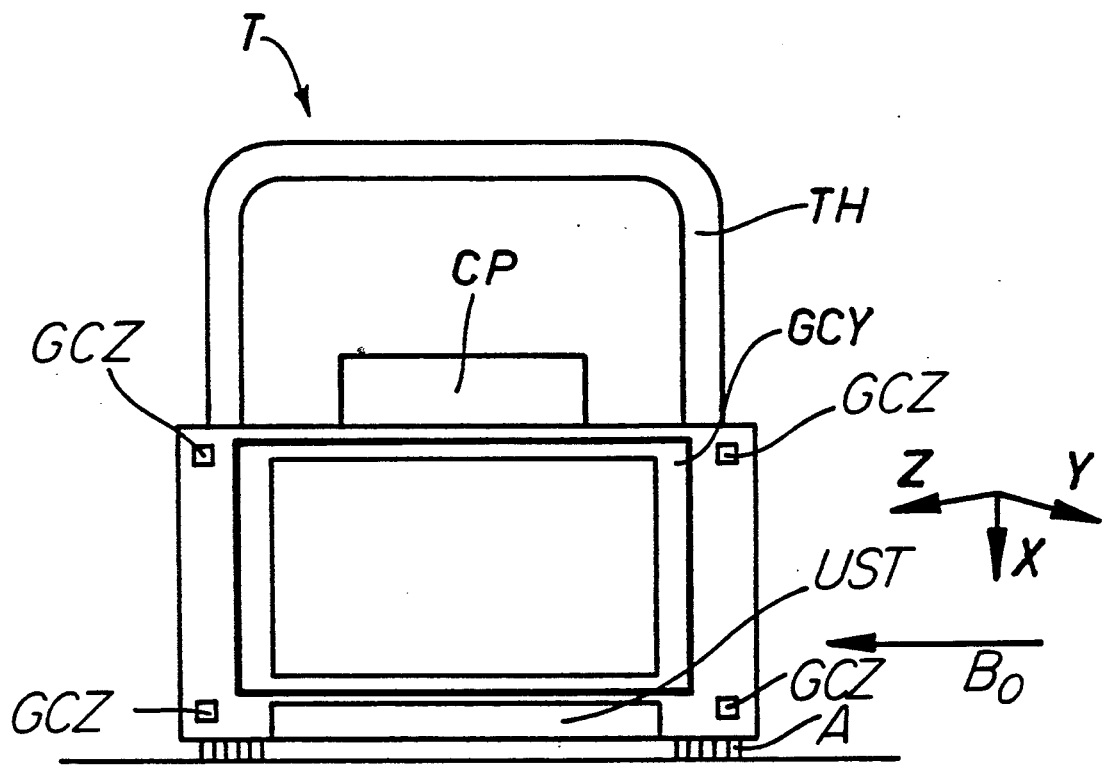
FIG. 2 shows in more detail the design of an examination probe, FIG. 3A
Figure 2:
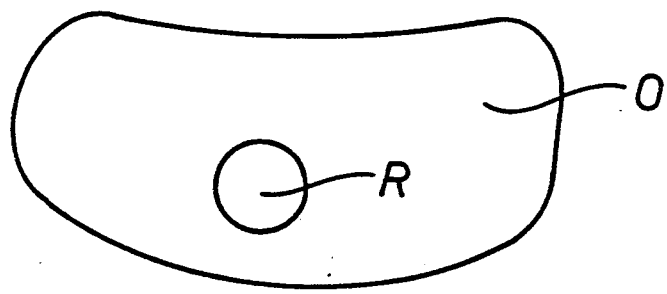

FIG. 2 shows in more detail the design of a sensor T, comprising a control panel CP, a handle TH, an ultrasonic sensor UST, gradient coils GCZ and GCY as well as means for emitting the magnetic fields associated with ESR and NMR functions and antenna equipment A required for receiving.

Figure 3A:
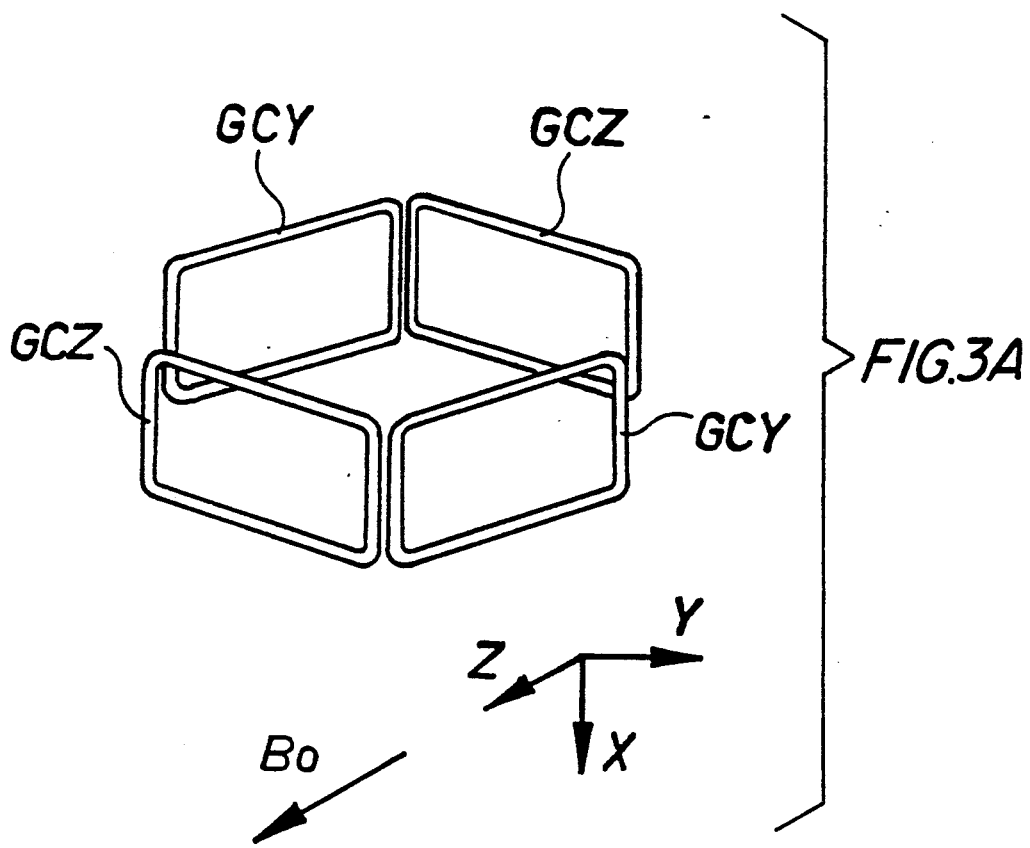
FIG. 3B shows a magnetic field produced by gradient field coils, shows the design of magnetic field gradient coils.
Figure 3B:
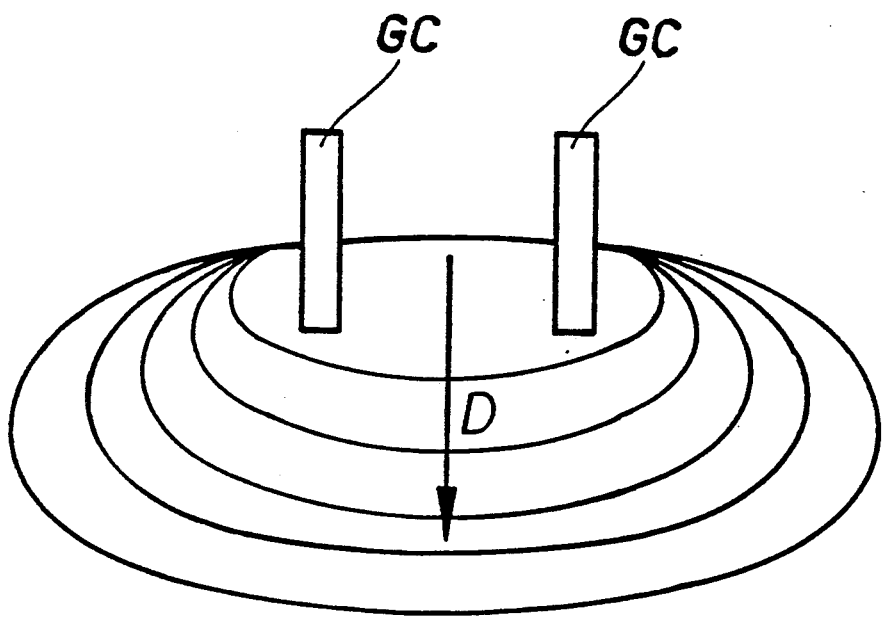

FIG. 3A shows in more detail one way of winding the gradient coils GCZ and GCY and the configuration of a generated gradient field as a function of a distance D, wherein D is the distance from the magnetic centre of the coils, as shown in FIG. 3B.

Figure 4:
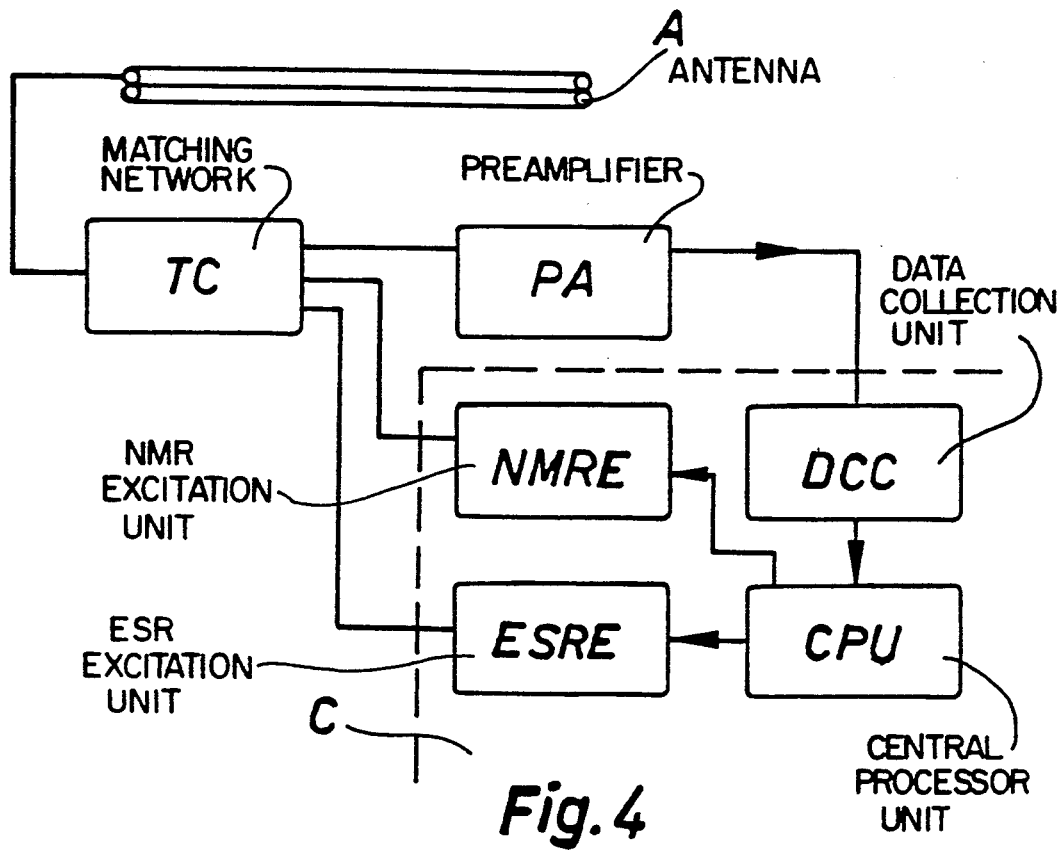
FIG. 4 shows the coupling of an NMR and ESR coil to a matching network, to a preamplifier and to excitation transmitters.

FIG. 4 shows in more detail the coupling of antenna equipment A included in ESR and NMR operation by way of a matching network TC to a preamplifier PA, an NMR excitation emitter NMRE and an ESR excitation emitter ESRE, controlled by a central processor unit CPU which also collects signal data through a data collection unit DCC.

Figure 5:
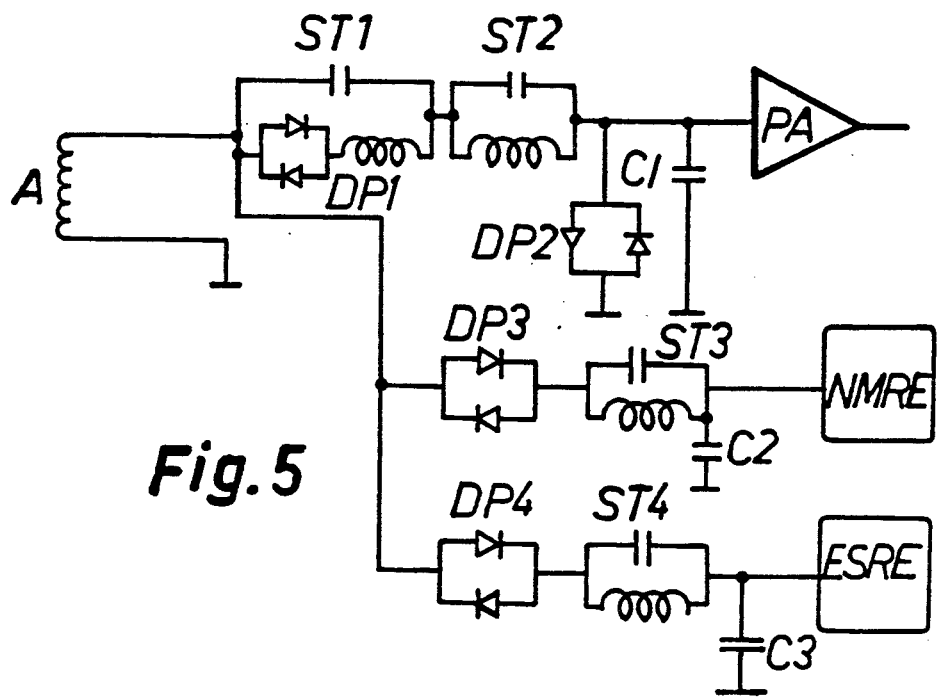
FIG. 5 shows a circuit diagram for the matching network, FIG. 6A

FIG. 5 is a more detailed view of the circuitry of matching network TC associated with antenna equipment A, wherein parallel resonance circuits ST1 and ST2 as well as a diode couple DP2 protect preamplifier PA during NMR and ESR excitation procedures. A diode couple DP1 switches the circuit ST1 excited to NMR frequency into a parallel resonance circuit on high NMR signal levels (excitation) and on low signal levels the inductance of antenna A as well as the series-connection of the capacitance of C1 and the capacitance of ST1 forms a parallel resonance circuit with A, which is excited to NMR signal frequency. A parallel resonance circuit ST3 is excited to ESR frequency and thus prevents emitter NMRE from loading emitter ESRE in connection with the saturation of an electron spin system. Diode couples DP3 and DP4 prevent the loading in connection with the detection of NMR signal. A parallel resonance circuit ST4 prevents emitter ESRE from loading during the excitation of a nuclear system. Capacitor C2 excites antenna A to the resonance in connection with NMR excitation and capacitor C3 in connection with electron spin saturation.

Figure 6A:
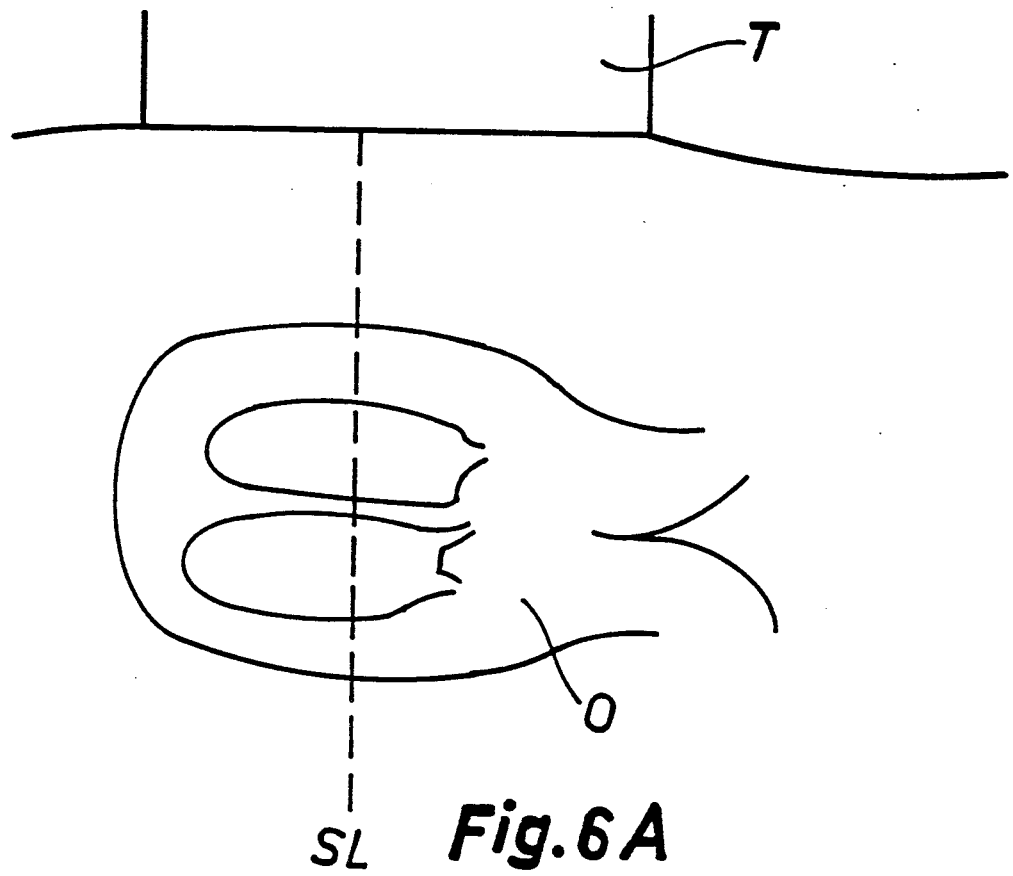
FIG. 6B shows the signal produced during examination, shows an application of the invention to the examination of the characteristics of a target volume.
Figure 6B:
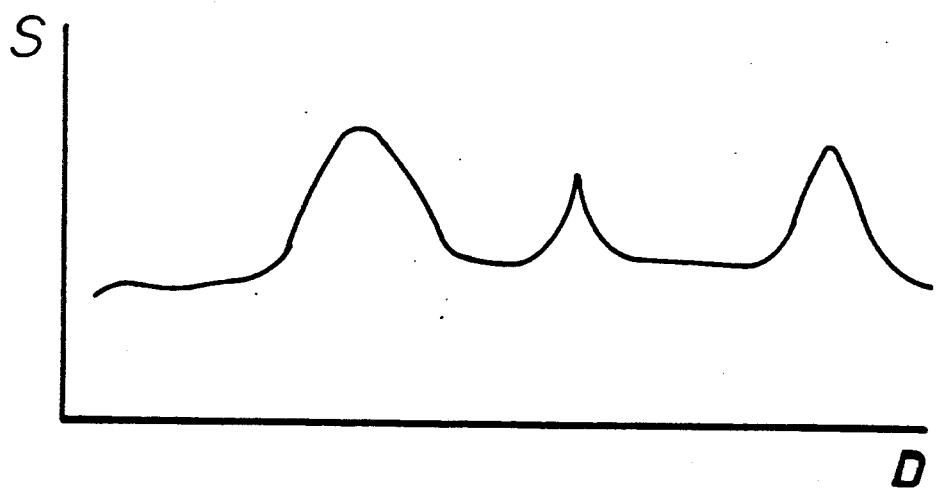

FIG. 6A illustrates the examination of an organ O by means of a so-called sensitive line method, the sensitive examination area is shown by a dashed line SL, the examination result obtained can be e.g. a signal intensity S along line SL as a function of distance D, as shown in FIG. 6B.

Figure 7:
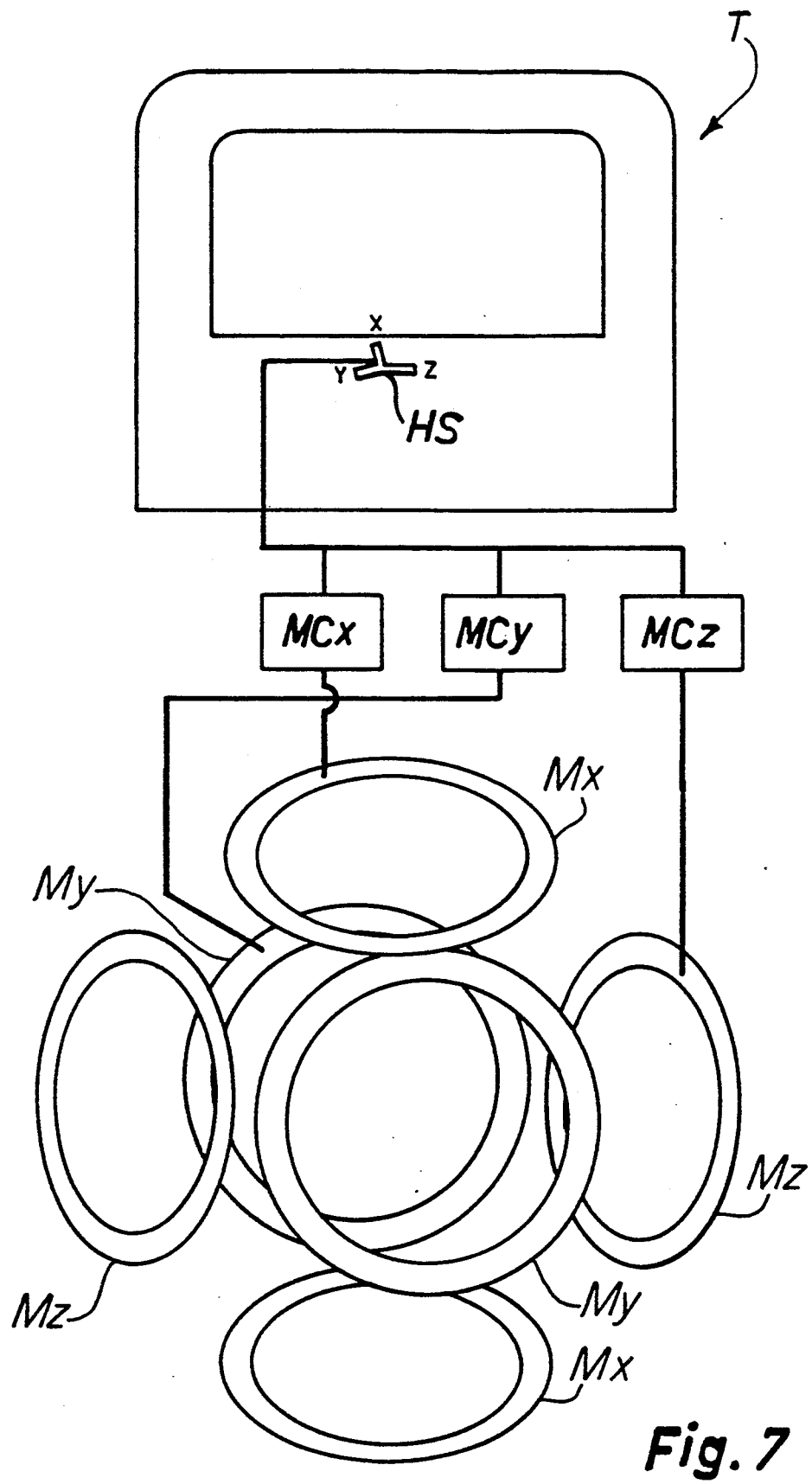
FIG. 7 shows the relationship of the direction of a sensor and the direction of a polarizing magnetic field.

FIG. 7 illustrates one way of directing a polarizing magnetic field Bo along the direction of a sensor. Sensor T is provided with three orthogonal Hall sensors HS for sensing the direction of the magnetic field Bo, which control sources of current MCx, MCy, MCz coupled to orthogonal magnetic coils Mx, My, Mz for adjusting the direction of the magnetic field Bo in a manner that magnetic field Bo always extends in a desired direction relative to sensor T so that the magnetic component of the electromagnetic radiation produced on the target area by antenna equipment A associated with the radiation of the electron spin system is as orthogonal as possible relative to the direction of the polarizing magnetic field.

Figure 8:
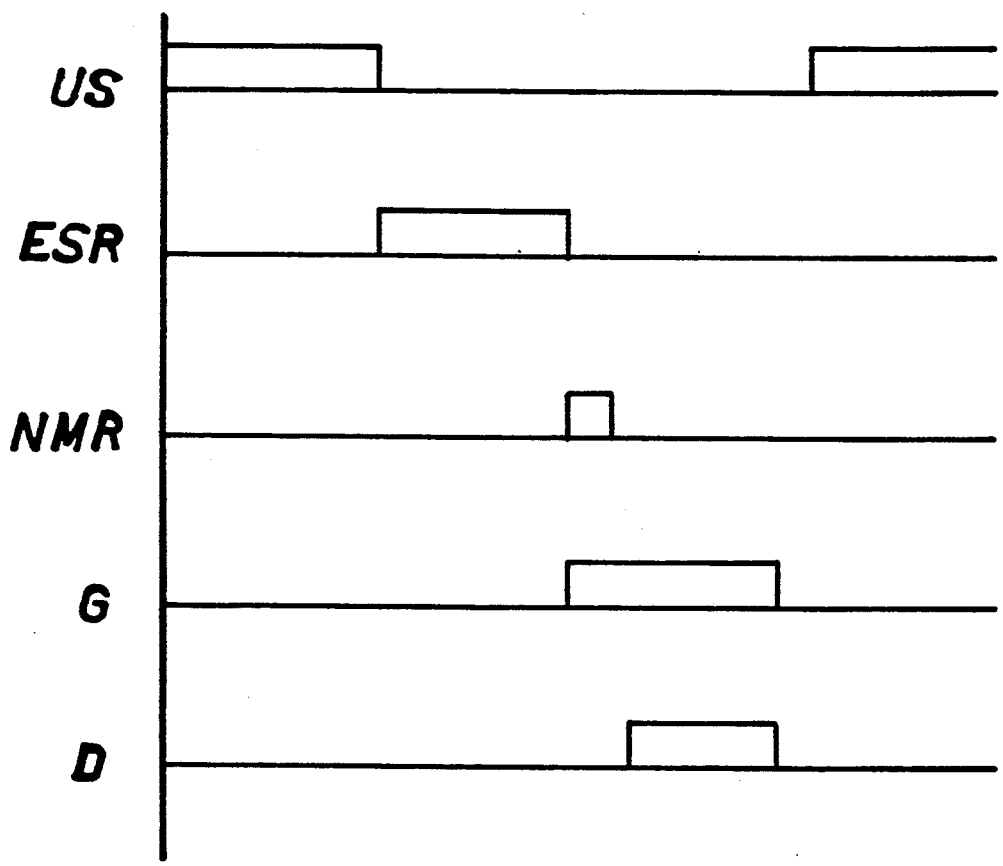
FIG. 8 is a flow chart for the action sequence.

FIG. 8 shows one action sequence: US represents the time of ultrasonic imaging, an ESR axis represents the time of electron spin saturation, an NMR axis represents the time of NMR excitation, a G axis includes the time of gradient functions and D is the time of NMR signal collection.

An examination effected by means of the apparatus, which closely resembles the examination described in reference Sepponen: U.S. Pat. No. 4,543,959, is carried out as follows. The examiner, a physician or the like, searches a body section (organ O) to be examined by means of an ultrasonic image shown on the display of central unit C. Organ O includes an interesting region R for whose characterization he or she needs NMR information (e.g. relaxation times T1 and T2). The patient has been or is injected with substances which relax an electron spin system and spread in tissues. Such substances has been described in reference Ettinger: U.S. Pat. No. 4,719,425. The electron spin system is saturated with a radiofrequency output produced by emitter ESRE for effecting a DNP phenomenon. The saturation of electron spins is stopped and NMR excitation and gradient operations are used to limit a region, e.g. a linear region, the NMR signal obtained therefrom being received by means of antenna A and processed by means of CPU for desired information.

As for its technical design, the ultrasonic imaging unit included in the apparatus can be a commercially available line sensor equipped device, manufactured e.g. by Siemens, West Germany; Aloka, Japan; Hitachi, Japan; Toshiba, Japan. The apparatus can have as its central unit e.g. an IBM AT microcomputer, manufactured by IBM, USA. The ESR and NMR components can be designed according to the prior art by using signal sources, manufactured by Hewlett Packard, USA, and power amplifiers, manufactured by ENI, USA. Gradient current sources can be e.g. those manufactured by Copley Controls Corp. (USA) and magnetic current sources e.g. those manufactured by Brucker GmbH (West Germany).

By means of the invention, heating or warming up of an object is avoided during radiation since the target area is limited. The NMR signal is not necessary worked into an image, whereby the required signal-to-noise ratio is low and thus the intensity of a polarizing magnetic field is low (less than 0.02 T) and the ESR radiation is only used just before the recording of an NMR signal. And, in addition, the intensity of a polarizing magnetic field can be changed between ESR and NMR operations by appropriate control of current source MC, as described in reference Sepponen: FI appln 883153 corresponding U.S. Pat. application Ser. No. 372,046 filed Jun. 27, 1989 now abandoned in favor of U.S. patent application Ser. No. 07/663,076, filed Feb. 28, 1991.

The invention can be applied e.g. to the measuring of blood circulation, to the determination of the blood content in cardiac muscle in various phases of the cardiac operation cycle, to tissue characterization, to the examination of liver activity, to the examination of foodstuffs, to the examination of test animals as well as to the examination of e.g. the absorption, effects and metabolism of pharmaceuticals.

The embodiments and applications of the invention are not limited to the above but a plurality of other applications and objects are conceivable.

I claim:

1. An apparatus for enabling an operator to carry out an examination of a target area within an object subjected to a polarizing magnetic field produced by a magnetic field generating means external of the object, said apparatus comprising:

means for transmitting ultrasonic energy to the target area and for receiving reflected ultrasonic energy therefrom for obtaining ultrasonic data from the target area;

NMR means including means for applying rf pulse signals to the target area, means for applying a magnetic field gradient to the target area, and means for receiving NMR signals from the target area;

means for supplying electron spin resonance energy to the target area for amplifying, by dynamic nuclear polarization, the NMR signals received from the target area; and said apparatus including a common unit freely movable by the operator' to a desired position with respect to the target area, said common unit containing at least a portion of said ultrasonic energy transmitting and receiving means, at least a portion of said NMR means, and at least a portion of said means for supplying electron spin resonance energy; said common unit including sensor means for sensing the direction of the polarizing magnetic field to which the object is subjected.

2. An apparatus as set forth in claim 1 further including means for adjusting the direction of the polarizing magnetic field responsive to said sensor means such that the polarizing magnetic field extends in a desired direction relative to said sensor means.

3. An apparatus as set forth in claim 2 wherein said means for applying a magnetic field gradient is fitted in said common unit.

4. An apparatus as set forth in claim 1 wherein said means for applying a magnetic field gradient is fitted in said common unit.

* * * * *